(12) United States Patent
Schmid

(10) Patent No.: US 8,017,645 B2
(45) Date of Patent: Sep. 13, 2011

(54) MELATONIN DAILY DOSAGE UNITS

(75) Inventor: Hans W. Schmid, Zug (CH)

(73) Assignee: ASAT AG Applied Science & Technology, Zug (CH)

(*) Notice: Subject to any disclaimer, the term of this patent is extended or adjusted under 35 U.S.C. 154(b) by 547 days.

(21) Appl. No.: 12/116,484

(22) Filed: May 7, 2008

(65) Prior Publication Data

US 2008/0293803 A1 Nov. 27, 2008

Related U.S. Application Data

(63) Continuation of application No. 10/533,517, filed as application No. PCT/EP03/12099 on Oct. 30, 2003, now abandoned, which is a continuation-in-part of application No. 10/353,056, filed on Jan. 29, 2003, now abandoned.

(30) Foreign Application Priority Data

Oct. 30, 2002 (DE) .................. 102 50 646

(51) Int. Cl.
A61K 31/13 (2006.01)
(52) U.S. Cl. ...................................... 514/419
(58) Field of Classification Search .................. None
See application file for complete search history.

(56) References Cited

U.S. PATENT DOCUMENTS

| 4,654,361 | A | | 3/1987 | Samples |
| 4,746,674 | A | * | 5/1988 | Pierpaoli et al. ............. 514/415 |
| 4,818,540 | A | | 4/1989 | Chien et al. |
| 5,006,004 | A | * | 4/1991 | Dirksing et al. ............. 401/261 |
| 5,577,636 | A | | 11/1996 | Fukuoka et al. |
| 5,637,606 | A | | 6/1997 | Matsumoto |
| 5,656,264 | A | | 8/1997 | Hanada |
| 5,750,107 | A | | 5/1998 | Nomura |
| 5,952,373 | A | | 9/1999 | Lanzendorfer et al. |
| 5,985,293 | A | | 11/1999 | Breton et al. |
| 6,007,834 | A | | 12/1999 | Merkus |
| 6,013,279 | A | | 1/2000 | Klett-Loch |
| 6,030,948 | A | | 2/2000 | Mann |
| 6,281,241 | B1 | * | 8/2001 | Elsner ......................... 514/415 |
| 6,524,619 | B2 | | 2/2003 | Pearson |
| 6,596,266 | B2 | | 7/2003 | Catalfo |
| 6,602,526 | B2 | | 8/2003 | Riley |
| 6,964,969 | B2 | | 11/2005 | McCleary |

(Continued)

FOREIGN PATENT DOCUMENTS

AT 367634 B 7/1982

(Continued)

OTHER PUBLICATIONS

Kljonowa et al., "Insecticidal and Mitcidal Preparations for Treating Animals", 2001, pp. 184-185 Weterinarnyie preparaty w Rossii, Sprawotschnik, Moskau, Selkhozizat.

(Continued)

Primary Examiner — Anand Desai
Assistant Examiner — Melissa Mercier
(74) Attorney, Agent, or Firm — Rothwell, Figg, Ersnt & Manbeck, P.C.

(57) ABSTRACT

The present invention relates to a disposable container for a medicament or cosmetic agent for topical application, containing a single dose of melatonin or of a melatonin derivative which corresponds to a locally effective dose but which does not cause any systemic effect.

29 Claims, 2 Drawing Sheets

U.S. PATENT DOCUMENTS

Figure 1C:
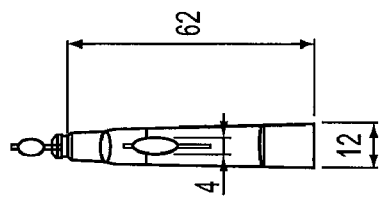

| | | |
|---|---|---|
| 2001/0031744 A1 | 10/2001 | Kosbab |
| 2005/0271692 A1 | 12/2005 | Gervasio-Nugent et al. |

FOREIGN PATENT DOCUMENTS

| | | |
|---|---|---|
| CN | 2223996 | 4/1996 |
| DE | 20019365 U1 | 2/2001 |
| DE | 101 10 418 A | 9/2002 |
| EP | 0150751 A1 | 8/1985 |
| EP | 0 867 181 A | 9/1998 |
| GB | 2079238 A | 1/1982 |
| GB | 2370504 A | 7/2002 |
| WO | 02069927 A1 | 9/2002 |
| WO | 03/049687 A2 | 6/2003 |

OTHER PUBLICATIONS

Database WPI Section CH, Week 199134, Derwent Publications, AN 1991-248680, Jul. 11, 1991, XP002270609.

Kobayashi et al, "Effect of Leaves of *Gingko biloba* on hair regrowth . . . ", Pharmaceutical Society of Japan, vol. 113, No. 10, Oct. 1, 1993, pp. 718-724.

\* cited by examiner

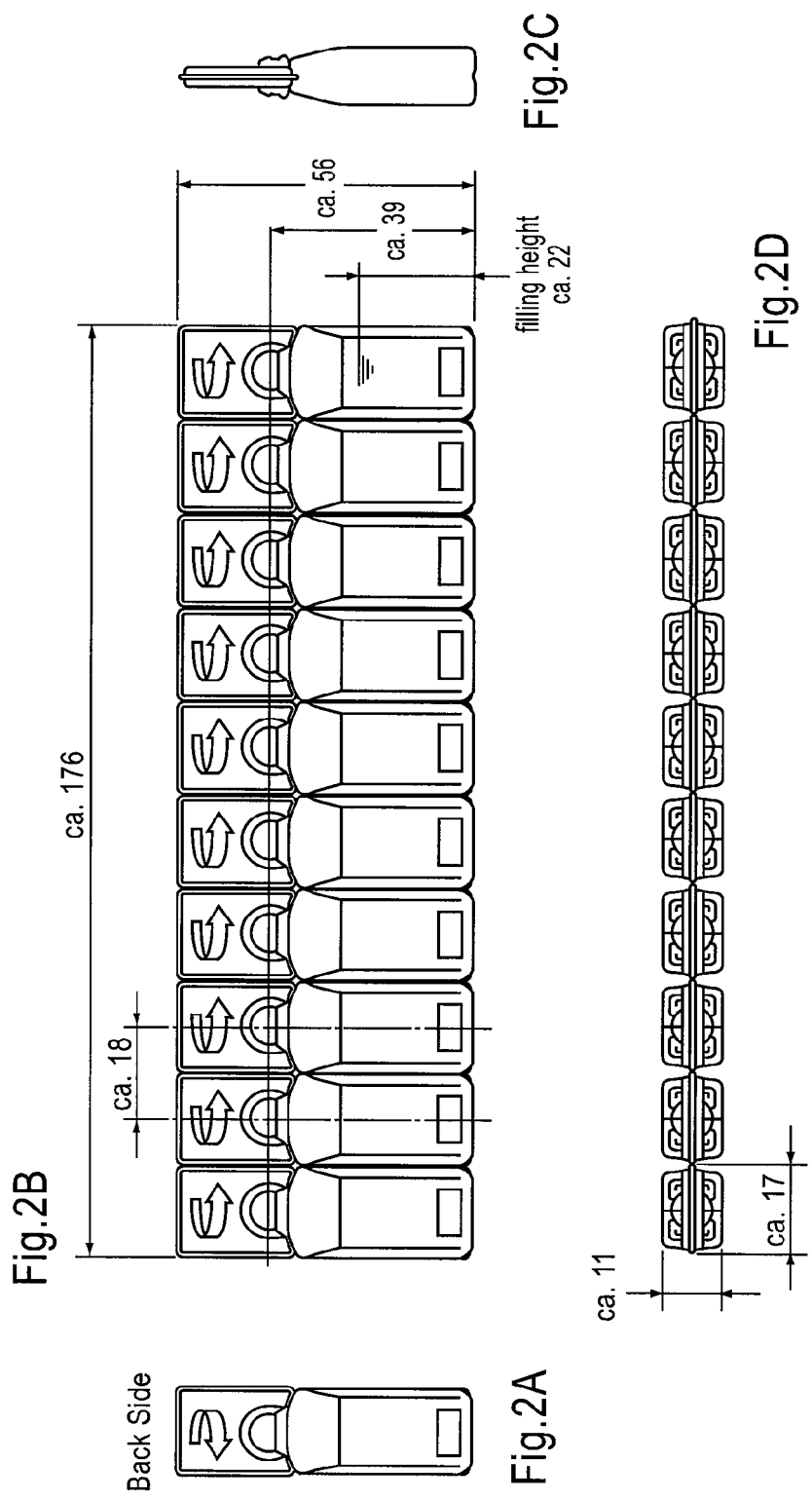

MELATONIN DAILY DOSAGE UNITS

This application is a continuation of U.S. Ser. No. 10/533,517 filed Aug. 17, 2005; which is a 35 U.S.C. 371 National Phase Entry Application from PCT/EP03/12099, filed Oct. 30, 2003, which is a continuation-in-part of 10/353,056 filed Jan. 29, 2003, which claims the benefit of German Patent Application No. 102 50 646.9 filed Oct. 30, 2002 and German Patent Application No. 202 17 814.5 filed on Nov. 18, 2002 the disclosures of which are incorporated herein in their entirety by reference.

The present invention relates to a disposable container for a medicament or cosmetic agent for topical application, containing a single dose of melatonin or of a melatonin derivative which corresponds to a locally effective dose but which does not cause any systemic effect.

Melatonin-containing agents can be used for various medical and cosmetic purposes. For example, the document DE 101 10 418.9 discloses melatonin-containing compositions for topical application on the skin and in the hair.

The subject of the present invention is a disposable container for a medicament or cosmetic agent for topical application, containing a single dose of melatonin or of a melatonin derivative which corresponds to a locally effective dose but which does not cause any systemic effect.

The disposable container according to the invention permits application of a dose of melatonin or of a melatonin derivative which is locally effective but which causes no undesired change in the normal melatonin plasma level. The single dose of melatonin or of melatonin derivative which is applied according to the invention causes no significant elevation of the melatonin plasma level for example.

The expression "melatonin or melatonin derivative", as it is used in the context of this application, includes melatonin and/or melatonin derivatives and salts, esters or complexes thereof. Preferred melatonin derivatives include, for example, 5-methoxytryptamine, 5-methoxytryptophan, 5-methoxytryptophol, 5-methoxy-indole-3-acetic acid and 6-hydroxymelatonin.

The single dose according to the invention represents a dose which permits a positive cosmetic and/or therapeutic effect without significant changes in the plasma level. According to the invention, a single dose of from approximately 0.001 to approximately 1.0 mg of melatonin is preferred, and more preferably a single dose of from approximately 0.01 to approximately 0.2 mg of melatonin. Depending on the application area or the intended use of the agent, a single dose can be applied once or several times daily. In a preferred embodiment, the single dose corresponds to a daily dose, particularly preferably a daily dose to be used in the evenings.

The medicament or cosmetic agent is preferably present as a liquid formulation. Examples of suitable formulations for topical application of the agent are solutions, suspensions, emulsions, microemulsions, nanosystems, creams, gels, lotions, sprays, foams or ointments, and any other formulation which can be applied topically. The agent is particularly preferably provided in the form of a cosmetic solution.

Depending on its intended use, the medicament or cosmetic agent contained in the disposable container according to the invention can have different concentrations of melatonin or of a melatonin derivative. The agent preferably contains a concentration of approximately 0.001 to approximately 0.01% (by weight), more preferably approximately 0.003 to 0.004% (by weight) of melatonin or of a melatonin derivative. A particularly preferred concentration is approximately 0.0033% (by weight).

In one embodiment, the therapeutic or cosmetic agent contains melatonin or a melatonin derivative as sole active substance. The agent can, however, also contain one or more further active substances such as vitamin A, vitamin A acid or other vitamin A derivatives, biotin and/or gingko biloba.

In a preferred embodiment, the medicament or cosmetic agent contains a combination of the active substances melatonin or melatonin derivative with biotin and/or gingko biloba. The active substances in this embodiment can be in different dosages. A particularly preferred dosage of this combination is from approximately 0.05 to approximately 0.2 mg, particularly preferably approximately 0.1 mg of melatonin or melatonin derivative, from approximately 0.2 to approximately 0.4 mg, particularly preferably approximately 0.3 mg of biotin, and from approximately 1.3 to approximately 1.7 mg, particularly preferably approximately 1.5 mg of gingko biloba. Gingko biloba can in this case be contained for example as an extract, in particular as a dry extract, and/or in the form of one or more ingredients.

In a further preferred embodiment, the agent contains a combination of the active substances melatonin or melatonin derivative and vitamin A, vitamin A acid or another derivative of vitamin A. In this preferred active substance combination, the dosage of melatonin or melatonin derivative is preferably from approximately 0.05 to 0.2 mg, particularly preferably approximately 0.1 mg of melatonin.

The medicament or cosmetic agent can also contain one or more cosmetic and/or pharmaceutical auxiliaries or additives, for example thickeners, minerals or perfumes.

The composition according to the invention can be used to promote hair growth, in particular to prevent and/or treat alopecia in men or in women. Particularly preferred indications are male pattern androgenetic alopecia, female pattern androgenetic alopecia, male pattern diffuse alopecia and female pattern diffuse alopecia.

Depending on the intended application or use, the disposable container according to the invention can contain different volumes of the medicament or cosmetic agent. In a preferred embodiment, the disposable container contains approximately 2.5 to approximately 3.5 ml, preferably approximately 2.9 to approximately 3.2 ml of the agent. A particularly preferred volume is approximately 3.0 ml.

The therapeutic or cosmetic agent can be filled into the container using any suitable method known in the prior art. The agent is preferably filled into the container under GMP conditions. In this way it is possible to ensure that the agent is sterile and that, when the agent is applied, no problems arise in respect of bacterial contamination.

The disposable container according to the invention can in principle be made of any desired material, in particular a material approved for packaging of food products and pharmaceutical products. Examples of preferred materials are plastics and mixtures of plastics. Examples of particularly suitable plastics are polyethylene, polyvinyl chloride, polystyrene, polypropylene, polycycloolefins or mixtures or copolymers thereof, with particular preference being given to polyethylene or polycycloolefins.

Depending on its desired outward appearance, the disposable container can be transparent, non-transparent, colorless or colored. Any desired dyes can for example be added to the plastic in order to obtain a colored container. A non-transparent container is preferred for use if the agent contains light-sensitive substances, because a non-transparent container additionally affords protection from light.

Figure 1D:
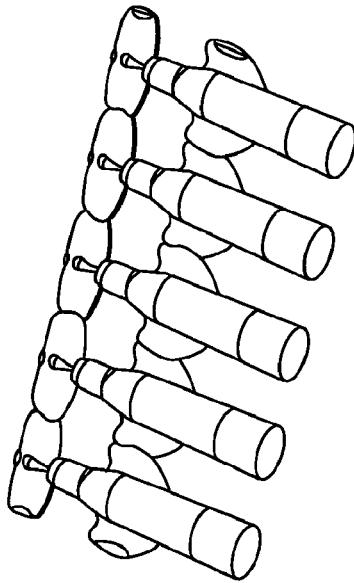
Figure 1A:
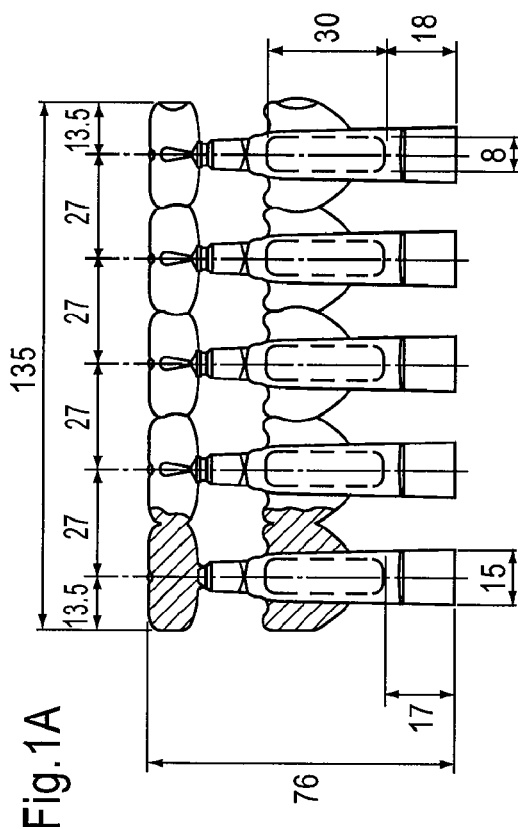
Figure 1B:
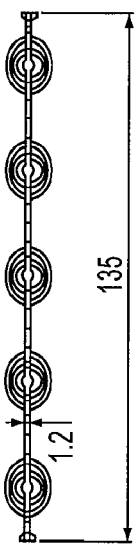

The disposable container according to the invention can in principle have any desired shape. Examples of preferred containers are shown in FIGS. 1 and 2. A suitable disposable container preferably comprises a part in which the agent is contained, and a disposable closure piece which is connected to the lower part via a predetermined break line.

Simple and safe handling of the container is advantageously ensured by the fact that it preferably has, on its head, a disposable closure piece which is opened by turning it. The container can thus be easily opened. In addition, after opening, the agent can emerge only if pressure is applied. This pressure can for example be exerted by hand during the application. This property allows the user to correctly dose the agent and position it in a targeted manner. If the agent is to be applied to the scalp or hair, the opened container can be guided directly through the hair like a comb. This permits straightforward and safe handling of the container and correct dosing of the agent.

Depending on the intended use, the disposable container carries lettering either printed on or embossed and/or is provided with a label.

Two or more disposable containers can furthermore be connected to one another in a detachable manner. For example, 5 or 10 containers are preferably connected to one another and form an arrangement. A container or an arrangement of containers can also be packed, preferably in a lightproof package, particularly preferably in an aluminum bag for example.

The expression "aluminum bag", as it is used here, includes bags made of aluminum and also bags which for example are coated with aluminum on the outside or inside. For example, bags made of one or more layers of plastic and/or paper can be coated with aluminum. A preferred bag comprises, for example, an aluminum-containing laminated foil which additionally includes polyethylene, polyester and/or paper.

A package, in particular a lightproof package, permits storage over a fairly long period of time without loss of efficacy of the agent. Furthermore, such a package can provide protection against gas loss.

Depending on the intended use, an aluminum bag in which one or more disposable containers are packed can be printed on and/or provided with a label.

In a further embodiment of the invention, a package unit comprising several arrangements of disposable containers is provided.

The invention is further explained by attached FIGS. 1 and 2 and examples.

FIG. 1 shows an arrangement of 5 disposable containers connected to one another in a detachable manner and in a preferred configuration.

1A shows a front view, 1B a plan view, 1C a side view, and 1D a perspective view obliquely from above.

FIG. 2A shows a front view of an individual disposable container in a preferred configuration.

2B shows a front view of an arrangement of 10 disposable containers connected to one another in a detachable manner, 2C shows a side view, and 2D shows a plan view of said arrangement.

EXAMPLES

Example 1

Composition of a Formulation According to the Invention Containing Melatonin, Gingko Biloba and Biotin as Active Substances The composition contains 0.05% by weight of gingko biloba dry extract, 0.01% by weight of biotin, 0.0033% by weight of melatonin and other additives, water, and ethanol. The pH of the composition is between 3.5 and 4.

Example 2

Clinical Study

The composition described in Example 1 was tested on 8 healthy female patients in a randomized double-blind study with placebo control and a crossover design. The daily dose was 0.1 mg of melatonin (3 ml of the composition) which was applied to the scalp each day before bedtime, for a period of 14 days.

Urine and blood samples were taken from the patients and were assayed for melatonin and the metabolite 6-hydroxymelatonin sulfate.

It was found that the melatonin plasma profiles of the patients treated with melatonin or placebo corresponded to the concentration/time profiles described in the literature for endogenous melatonin. This confirms that topical application of the melatonin-containing composition for 14 days does not alter endogenous melatonin secretion.

Administration of the composition for 14 days did not increase the plasma concentration of melatonin, or the concentration of 6-hydroxymelatonin sulfate in urine, above physiological concentrations. Topical application of the melatonin-containing composition was not associated with side effects. Nor were any effects found on reaction times or on cortical excitation parameters.

All things considered, it must be concluded that administration of the composition does not induce any systemic effects.

The invention claimed is:

1. A method for promoting hair growth and/or treating alopecia in a human subject in need of such hair growth and/or treatment of alopecia, comprising, applying to the scalp or hair of the human subject a single dose of melatonin or melatonin derivative selected from the group consisting of 5-methoxytryptamine, 5-methoxytryptophan, 5-methoxytryptophol, 5-methoxyindole-3-acetic acid and 6-hydroxymelatonin, or salts or esters thereof, which corresponds to a locally effective dose but which does not cause any systemic effect, wherein the single dose is contained in a disposable container and wherein the disposable container contains only the single dose and the single dose corresponds to a daily dose of 0.01 to 0.2 mg of melatonin or melatonin derivative.

2. A method according to claim 1, wherein the alopecia is selected from the group consisting of male pattern androgenetic alopecia, female pattern androgenetic alopecia, male pattern diffuse alopecia and female pattern diffuse alopecia.

3. The method of claim 1, wherein the single dose is present as a liquid formulation.

4. The method of claim 3, wherein the liquid formulation has a concentration of 0.001 to 0.01% (by weight) of melatonin.

5. The method of claim 4, characterized in that the liquid formulation has a concentration of 0.003 to 0.004% (by weight) of melatonin.

6. The method of claim 1, wherein the single dose contains, as sole active substance, melatonin or a melatonin derivative.

7. The method of claim 1, wherein the single dose contains, as active substances, a combination of melatonin or a melatonin derivative together with biotin and/or gingko biloba.

8. The method of claim 1, wherein the single dose contains, as active substance, a combination of melatonin or a melatonin derivative and vitamin A, or vitamin A acid.

9. The method of claim 1, wherein the container contains 2.5 to 3.5 ml of the agent.

10. The method of claim 9, wherein the container contains 2.9 to 3.2 ml of the agent.

11. The method of claim 1, wherein the single dose is filled into the container under GMP conditions.

12. The method of claim 1, wherein the container is made of a plastic.

13. The method of claim 12, wherein the container is made of polyethylene, polypropylene, polyvinyl chloride, polystyrene or a mixture of these.

14. The method of claim 1, characterized in that the container is colorless.

15. The method of claim 1, wherein the container is colored.

16. The method of claim 1, wherein the container is transparent.

17. The method of claim 1, wherein the container is non-transparent.

18. The method of claim 1, wherein the container has, on its head, a disposable closure piece which is opened by turning it.

19. The method of claim 18, wherein after opening, the single dose emerges only when pressure is applied.

20. The method of claim 1, wherein the container carries lettering either printed on or embossed and/or is provided with a label.

21. The method of claim 1, wherein the container is comprised of an arrangement of containers which are connected to one another in a detachable manner.

22. The method of claim 21, wherein 5 containers are connected to one another in a detachable manner.

23. The method of claim 21, wherein 10 containers are connected to one another in a detachable manner.

24. The method of claim 21, wherein the container is packed into an aluminum bag.

25. The method of claim 24, wherein the bag consists of an aluminum-containing laminated foil and additionally includes polyethylene, polyester and/or paper.

26. The method of claim 25, wherein the aluminum bag is printed on and/or is provided with a label.

27. A method for promoting hair growth and/or treating androgenetic and diffuse alopecia in a human male subject in need of such hair growth and/or treatment of alopecia, comprising, applying to the scalp or hair of the human subject a single dose of melatonin or melatonin derivative selected from the group consisting of 5-methoxytryptamine, 5-methoxytryptophan, 5-methoxytryptophol, 5-methoxyindole-3-acetic acid and 6-hydroxymelatonin, or salts or esters thereof, which corresponds to a locally effective dose but which does not cause any systemic effect, wherein the single dose is contained in a disposable container and wherein the single dose corresponds to a daily dose.

28. The method of claim 27, wherein the single dose is 0.001 to 1.0 mg of melatonin or melatonin derivative.

29. The method of claim 28, wherein the single dose is 0.01 to 0.2 mg of melatonin or melatonin derivative.

* * * * *